United States Patent [19]

Toja et al.

[11] Patent Number: 5,053,416
[45] Date of Patent: Oct. 1, 1991

[54] DERIVATIVES OF 1,2,5,6-TETRAHYDROPYRIDINE SUBSTITUTED BY A THIAZOLYL OR OXAZOLYL RADICAL, THEIR USE AS MEDICAMENTS AND COMPOSITIONS CONTAINING THEM

[75] Inventors: Emilio Toja, Milan; Carla Bonetti, Fontanella; Fernando Barzaghi; Giulio Galliani, both of Monza, all of Italy

[73] Assignee: Roussel Uclaf, Paris, France

[21] Appl. No.: 457,566

[22] Filed: Dec. 27, 1989

[30] Foreign Application Priority Data

Dec. 28, 1988 [IT] Italy .................. 23121 A/88

[51] Int. Cl.$^5$ .................. A61K 31/44; C07D 413/04
[52] U.S. Cl. .................. 514/340; 514/342; 546/275; 546/280
[58] Field of Search ........... 546/280, 275; 514/340, 514/342

[56] References Cited

U.S. PATENT DOCUMENTS

| | | | |
|---|---|---|---|
| 3,004,979 | 10/1961 | Druey et al. | 546/338 |
| 4,710,508 | 12/1987 | Bergmeier | 514/357 |
| 4,866,077 | 9/1989 | Bogeso et al. | 546/276 |
| 4,902,699 | 2/1990 | Toja | 546/338 |

FOREIGN PATENT DOCUMENTS

| | | |
|---|---|---|
| 0725663 | 1/1966 | Canada . |
| 0296721 | 12/1988 | European Pat. Off. . |
| 307141 | 3/1989 | European Pat. Off. . |
| 0307141 | 3/1989 | European Pat. Off. . |
| 1258847 | 3/1961 | France . |

OTHER PUBLICATIONS

Jaffe, Journal of the American Chemical Society, vol. 76, No. 13, Jul. 5, 1954, pp. 3527-3531.
Chemical Abstracts, vol. 92, No. 13, Mar. 31, 1980, p. 641, Abstract No. 110798Y.

Primary Examiner—Jane T. Fan
Attorney, Agent, or Firm—Stevens, Davis Miller & Mosher

[57] ABSTRACT

Compounds of formula (I)

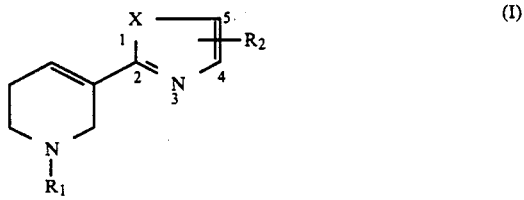

in which X represents oxygen or sulphur, $R_1$ represents hydrogen, a linear, branched or cyclic alkyl containing up to 8 carbon atoms, an alkenyl or alkynyl containing up to 6 carbon atoms, hydroxyl, an $OCOalk_1$ radical in which $alk_1$ represents alkyl containing up to 6 carbon atoms, an $OCONHalk_2$ radical in which $alk_2$ represents alkyl containing up to 6 carbon atoms, a $CO_2alk_3$ radical in which $alk_3$ represents alkyl or alkenyl containing up to 6 carbon atoms, an $Oalk_4$ radical in which $alk_4$ represents alkyl containing up to 6 carbon atoms, an $OCOAr_1$, $OCONHAr_2$ or $CO_2Ar_3$ radical in which $Ar_1$, $Ar_2$ or $Ar_3$ represents aryl containing up to 14 carbon atoms, $R_2$ represents hydrogen, a linear, branched or cyclic alkyl containing up to 6 carbon atoms, alkenyl or alkynyl containing up to 6 carbon atoms, an alkoxyalkyl $alk'_1Oalk'_2$ radical in which $alk'_1$ and $alk'_2$ represent alkyl containing up to 6 carabon atoms, hydroxyalkyl in which the alkyl contains up to 6 carbon atoms or aryl containing up to 14 carbon atoms, as well as their addition salts with organic or mineral acids, which compounds are useful in the treatment of patients suffering from Alzheimer's disease, senile dementia or memory disorders of the aged; also, compositions containing the same, method of use, method of preparation, and intermediates therefor.

9 Claims, No Drawings

DERIVATIVES OF 1,2,5,6-TETRAHYDROPYRIDINE SUBSTITUTED BY A THIAZOLYL OR OXAZOLYL RADICAL, THEIR USE AS MEDICAMENTS AND COMPOSITIONS CONTAINING THEM

The present invention relates to new derivatives of 1,2,5,6-tetrahydropyridine substituted by a thiazolyl or oxazolyl radical, their preparation process and intermediates, their use as medicaments and compositions containing them.

A subject of the invention is the compounds of formula (I):

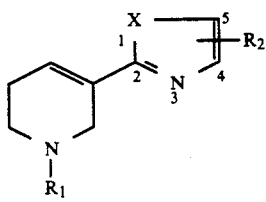

in which X represents oxygen or sulphur, $R_1$ represents hydrogen, a linear, branched or cyclic alkyl containing up to 8 carbon atoms, an alkenyl or alkynyl containing up to 6 carbon atoms, hydroxyl, an $OCOalk_1$ radical in which $alk_1$ represents alkyl containing up to 6 carbon atoms, an $OCONHalk_2$ radical in which $alk_2$ represents alkyl containing up to 6 carbon atoms, a $CO_2alk_3$ radical in which $alk_3$ represents alkyl or alkenyl containing up to 6 carbon atoms, an $Oalk_4$ radical in which $alk_4$ represents alkyl containing up to 6 carbon atoms, an $OCOAr_1$, $OCONHAr_2$ or $CO_2Ar_3$ radical in which $Ar_1$, $Ar_2$ or $Ar_3$ represents aryl containing up to 14 carbon atoms, $R_2$ represents hydrogen, a linear, branched or cyclic alkyl containing up to 6 carbon atoms, alkenyl or alkynyl containing up to 6 carbon atoms, an alkoxyalkyl $alk'_1Oalk'_2$ radical in which $alk'_1$ and $alk'_2$ represent alkyl containing up to 6 carbon atoms, hydroxyalkyl in which the alkyl contains up to 6 carbon atoms or aryl containing up to 14 carbon atoms, as well as their addition salts with organic or mineral acids.

Among the addition salts with acids, there can be cited those formed with mineral acids, such as hydrochloric, hydrobromic, sulphuric or phosphoric, or those formed with organic acids such as formic, acetic, propionic, benzoic, maliec, fumaric, succinc, tartaric, citric, oxalic, glyoxylic, aspartic, alkanesulphonic such as methane- or ethane-sulphonic, aryl-sulphonic such as benzene- or paratoluenesulphonic.

In the definition of the compounds of general formula (I), when one of the substituents represents alkyl, it is preferably methyl, ethyl, n-propyl, isopropyl, n-butyl, sec-butyl, tertbutyl or isobutyl. When one of the substituents represents alkenyl or alkynyl, it is preferably a vinyl, allyl, ethynyl or propynyl radical.

A particular subject of the invention is the compounds in which $R_1$ represents hydroxy, as well as their addition salts with mineral or organic acids, those in which $R_1$ represents hydrogen, as well as their addition salts with organic or mineral acids, as well as those in which $R_1$ represents a linear, branched or cyclic alkyl such as for example methyl, as well as their addition salts with organic or mineral acids.

Among the preferred compounds of the invention, there can be cited the compounds in which X represents oxygen as well as their addition salts with organic or mineral acids.

Among the preferred compounds of the invention, there can also be cited the compounds in which $R_2$ represents hydrogen and those in which $R_2$ represents a linear, branched or cyclic alkyl containing up to 6 carbon atoms, such as for example methyl as well as their addition salts with organic or mineral acids.

Among the preferred compounds of the invention, there can be cited the compounds in which X represents sulphur and $R_2$ represents a linear, branched or cyclic alkyl such as for example methyl, as well as their addition salts with organic or mineral acids.

In particular, a subject of the invention is the compounds of which the preparation is given hereafter in the Examples and quite particularly 1-hydroxy-3-(oxazol-2-yl)-1,2,5,6-tetrahydropyridine, 3-(oxazol-2-yl)-1,2,5,6-tetrahydropyridine, 3-(4-methyloxazol-2-yl)-1,2,5,6-tetrahydropyridine, and 3-(5-methyloxazol-2-yl)-1,2,5,6-tetrahydropyridine, and their addition salts with organic or mineral acids.

The compounds of the invention offer very useful pharmacological properties and in particular, a significant central cholinomimetic activity, by oral route, of lasting action.

Therefore, a subject of the invention is the products of the invention as medicaments, useful notably in the treatment of Alzheimer's disease or of senile dementia and also in the treatment of memory disorders of the aged.

More particularly, a subject of the invention, is as medicaments, the compounds of Examples 2, 6, 8 and 10.

The usual posology is variable according to the affection in question, the patient treated and the administration route. It can be between 1 mg and 100 mg per day, preferably between 1 mg and 20 mg per day, for example, between 1 and 15 mg per day in one or more doses for the product of Examples 6 and 10 administered by oral route.

Also a subject of the present invention is pharmaceutical compositions containing as active principle at least one product of formula (I). The pharmaceutical compositions of the invention can be solid or liquid and can be presented in the pharmaceutical forms currently used in human medicine, for example, plain or sugar-coated tablets, capsules, granules, suppositories and injectable preparations; they are prepared according to the usual methods.

The active principle or principles can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

Also, a subject of the invention is a process, characterized in that a compound of formula (II):

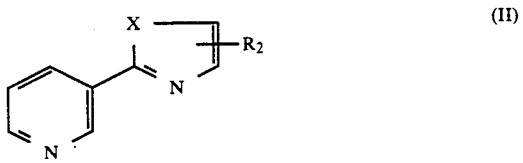

in which $R_2$ and $X$ have the previous significance, is subjected to the action of a compound of formula (III):

   (III)

in which $R'_1$ can take all of the values given above for $R_1$ with the exception of hydrogen, so as to obtain the compound of formula (IV):

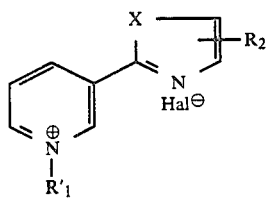   (IV)

which is subjected to the action of a reducing agent so as to obtain the compound of formula ($I_A$):

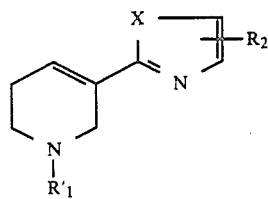   ($I_A$)

which, if desired, is salified, or is subjected, if desired, to the action of a cleaving agent of the $R'_1$ group so as to obtain the compound of formula ($I_B$):

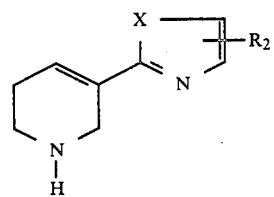   ($I_B$)

which, if desired, is salified or is subjected, to the action of an oxidation agent so as to obtain a compound of formula (I) in which $R_1$ represents an $OR''_1$ group, in which $R''_1$ represents a protector group of the hydroxy radical which is salified, if desired, or, if desired, the protector group is eliminated so as to obtain a compound of formula (I) in which $R_1$ represents a free hydroxy which, if desired, is salified.

In a preferred method of carrying out the process of the invention:
the compound of formula (III) used is an iodide,
the reducing agent is sodium borohydride,
the cleavage agent of the $R'_1$ group is alphachloroethyl chloroformate,
the oxidation agent is for example a peroxide such as benzoyl peroxide or bis(diphenyl-phosphinyl) peroxide,
the elimination of the protector group of the hydroxy radical is carried out in the usual way. An alkali metal is used for example, such as sodium in a lower alcohol such as methanol or ethanol or 1N sulphuric acid in the same solvents.

The compound of formula (II) in which $X$ is sulphur and $R_2$ methyl in position 4 is known, and it can be prepared according to the preparation process of 3-(4-methyl-thiazol-2-yl)-pyridine described in Helv. Chim. Acta. 28, 820 (1945).

The compounds of formula (II) in which $X$ is sulphur, carrying a substituent in position 4, can be prepared according to the reaction scheme:

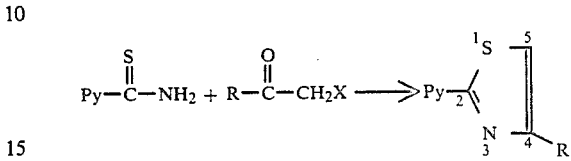

wherein
Py=3-pyridyl; $X_1$=Cl, Br.

The compounds of formula (II) in which $X$ is oxygen, carrying a substituent in position 4, can be prepared according to the reaction scheme:

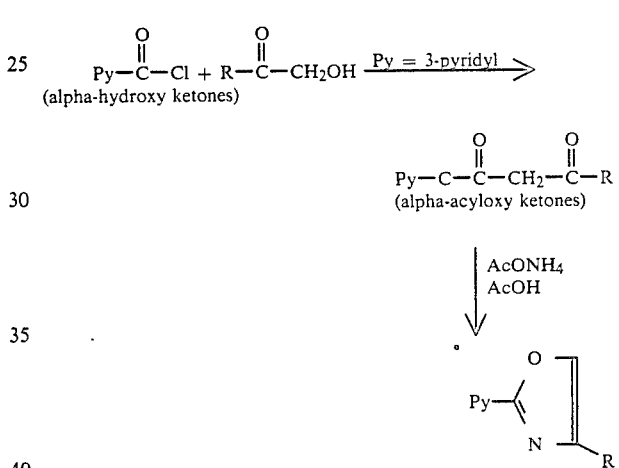

The compound of formula (II) in which $X$ is an oxygen atom and $R_2$ methyl in position 4 is a new product and is itself a subject of the present invention.

It can be prepared according to the process described above or also according to the process described hereafter in the Examples which can be summarized as follows:

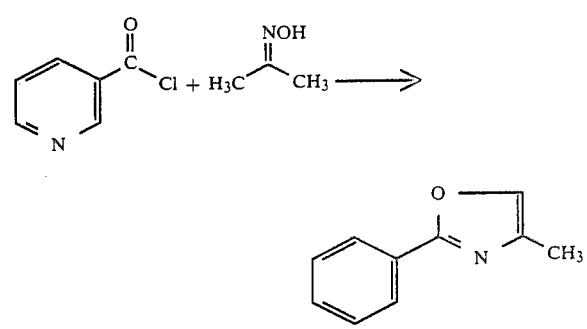

The compounds of formula (II) in which $X$ is oxygen, carrying a substituent in position 5, can be prepared according to the reaction scheme:
wherein
Py=3-pyridyl; $X_1$=Cl, Br.

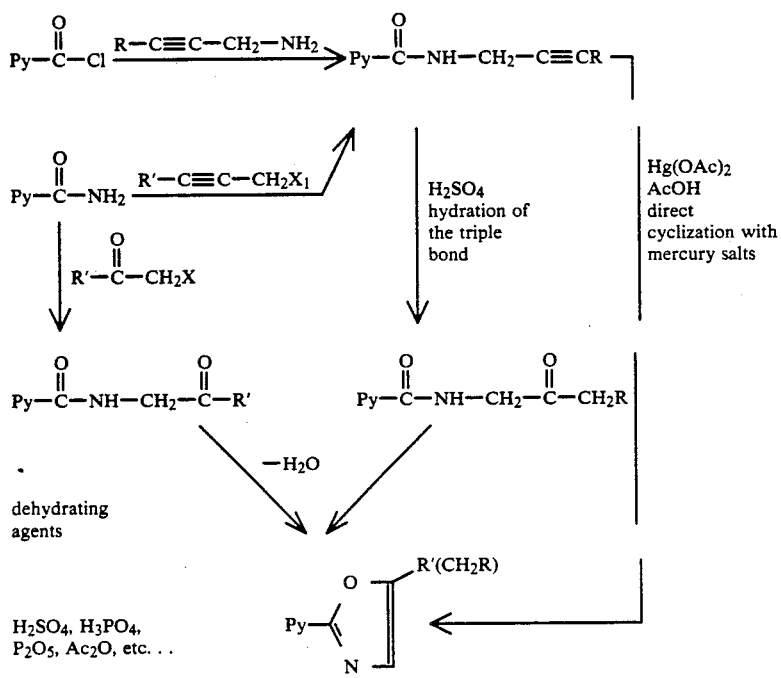

The examples which follow illustrate the invention without however limiting it.

EXAMPLE 1

1-methyl-3-(4-methyloxazol-2-yl)-1,2,5,6-tetrahydropyridine and its hydrochloride

STAGE A 1-methyl-3-(4-methyloxazol-2-yl)-pyridinium iodide.

10.8 g of 3-(4-methyloxazol-2-yl)-pyridine and 19.4 g of methyl iodide are mixed together in 140 cm³ of ethanol, then heated under reflux for 6 hours. The solvent is evaporated, the residue is crystallized from a mixture of ethanol and ether and 17 g of expected product is obtained, which is recrystallized from ethanol.

M.p.=203° C.

Analysis: $C_{10}H_{11}IN_2O$ Calculated: C % 39.76 H % 3.67 N % 9.27; Found: 39.47 3.74 9.15.

STAGE B 1-methyl-3-(4-methyloxazol-2-yl)-1,2,5,6-tetrahydropyridine and its hydrochloride.

4.7 g of sodium borohydride is added at 0° C. to 17 g of product obtained in Stage A in 200 cm³ of methanol. The mixture is allowed to return to ambient temperature and agitated for 3 hours. The solvent is evaporated, the residue is taken up in water, and extracted with ethyl acetate; the extracts are purified by chromatography on silica (eluant: chloroform-methanol 9-1), distilled at 110° C. under 0.05 mbar and 5.3 g of product is recovered in the form of a base, to which is added 96 cm³ of a 0.1N aqueous solution of hydrochloric acid. After concentrating to dryness, and crystallizing from an ethanol-ether mixture, 1.9 g of the expected hydrochloride is obtained.

M.p.=228°–230° C.

Analysis: $C_{10}H_{14}N_2O$, HCl Calculated: C % 55.94 H % 7.04 N % 13.05; Found: 55.79 7.18 12.97.

Preparation 1: [3-(4-methyloxazol-2-yl)-pyridine]

30 g of nicotinoyl chloride is added to 5.1 g of cooled acetoxime, then the mixture is heated to 130° C. The exothermic reaction mixture is maintained under agitation for 6 hours at 140° C. After cooling, iced water is added, followed by alkalizing with sodium carbonate and extracting with methylene chloride. The solvent is evaporated, the residue is taken up with ether and filtered; the solvent is evaporated and the residue is distilled at 150° C. under 0.08 mbar. 3.5 g of expected product is obtained which is purified by chromatography on silica (eluant: cyclohexane-ethyl acetate 7-3), with further distillation. After cooling, a solid product is obtained.

M.p.=40° C.

Analysis: $C_9H_8N_2O$ Calculated: C % 67.49 H % 5.03 N % 17.49; Found: 67.13 5.12 17.26.

EXAMPLE 2

3-(4-methyloxazol-2-yl)-1,2,5,6-tetrahydropyridine hydrochloride 3.25 g of alpha-chloroethyl chloroformate is added at −5° C. under inert atmosphere to a solution of 3.65 g of [1-methyl-3-(4-methyl-oxazol-2-yl)-1,2,5,6-tetrahydropyridine] in 70 cm³ of dichloroethane, and the mixture is heated under reflux for 2 hours. The solvent is evaporated, the residue is taken up in ether, filtered, the solvent is evaporated, the residue is taken up in 30 cm³ of methanol, heated under reflux for 45 minutes and the solvent is eliminated. After crystallization from ethanol, 1.9 g of expected product is obtained.

M.p.=276° C. (decomp.).

Analysis: $C_9H_{12}N_2O$, HCl Calculated: C % 53.87 H % 6.53 N % 13.96; Found: 53.61 6.66 13.76.

EXAMPLE 3

1-methyl-3-(4-methylthiazol-2-yl)-1,2,5,6-tetrahydropyridine and its hydrochloride

STAGE A 1-methyl-3-(4-methylthiazol-2-yl)-pyridinium iodide.

8.3 g of [3-(4-methylthiazol-2-yl)-pyridine] and 4.5 cm³ of iodomethane in 30 cm³ of ethanol are left in darkness for 10 days. After filtering, 14.6 g of product is obtained which is recrystallized from ethanol. M.p.=184°-186° C.

Analysis: $C_{10}H_{11}IN_2S$ Calculated: C % 37.75 H % 3.49 N % 8.80; Found: 37.49 3.43 8.71.

STAGE B 1-methyl-3-(4-methylthiazol-2-yl)-1,2,5,6-tetrahydropyridine and its hydrochloride.

Maintaining the temperature lower than 10° C., 2.57 g of sodium borohydride is added to 14.4 g of product obtained in Stage A in 100 cm³ of methanol. After agitating the mixture for 2 hours at ambient temperature, and concentrating to dryness, the residue is taken up in water and extracted with ethyl acetate; the extracts are dried and the solvent is evaporated. The residue is chromatographed on silica (eluant: methylene chloride-methanol 9-1), distilled at 140° C. under 0.007-0.008 mbar and 5.5 g of expected product is recovered in the form of a base. 1.57 g of base is dissolved in 5 cm³ of ethanol, 10. cm³ of 0.1N hydrochloric acid is added, followed by concentrating to dryness and crystallizing from isopropanol. 1.79 g of expected hydrochloride is obtained. M.p.=199°-202° C. (decomp.).

Analysis: $C_{10}H_{14}N_2S$, HCl Calculated: C % 52.05 H % 6.12 N % 12.14; Found: 52.18 6.23 12.06.

EXAMPLE 4

3-(4-methylthiazol-2-yl)-1,2,5,6-tetrahydropyridine hydrochloride 3.64 g of [1-methyl-3-(4-methylthiazol-2-yl)-1,2,5,6-tetrahydropyridine] is dissolved in 70 cm³ of dichloroethane, 2.95 g of alphachloroethyl chloroformate is added at 0° C. under inert atmosphere, and the whole is heated under reflux for one hour 30 minutes. The solvent is eliminated, te residue is taken up with ether and filtered. The filtrate is concentrated to dryness, the residue is taken up in 40 cm³ of methanol and heated for 30 minutes under reflux. The solvent is eliminated and the residue is crystallized twice from ethanol and ether and 2.67 g of expected product is obtained. M.p.=184°-188° C. (decomp.).

Analysis: $C_9H_{12}N_2S$, HCl Calculated: C % 49.88 H % 6.05 N % 12.93; Found: 49.71 5.97 13.04.

EXAMPLE 5

1-methyl-3-(oxazol-2-yl)-1,2,5,6-tetrahydropyridine and its hydrochloride

STAGE A 1-methyl-3-(oxazol-2-yl)-pyridinium iodide.

11.3 g of [(oxazol-2-yl)-pyridine] prepared as indicated in Helv. Chim. Acta 45 375 (1962) and 22.4 g of methyl iodide in 50 cm³ of ethanol are heated under reflux for 2 hours then the reaction medium is left for 2 days. The solvent is evaporated, the residue is crystallized from 95° ethanol and 17 g of product is obtained. M.p.=241° C. (decomp.) after recrystallization from ethanol.

Analysis: $C_9H_9IN_2O$ Calculated: C % 37.52 H % 3.15 N % 9.72; Found: 37.29 3.12 9.56.

STAGE B 1-methyl-3-(oxazol-2-yl)-1,2,5,6-tetrahydropyridine and its hydrochloride.

4.85 g of sodium borohydride is added at 0° C. to 16.7 g of product prepared in Stage A in 200 cm³ of methanol. The reaction is continued at ambient temperature for one hour, followed by evaporating to dryness. The residue is taken up in water, extracted with ethyl acetate and the extracts are dried and concentrated to dryness. After purifying by chromatography on silica (eluant: chloroform-methanol 9-1) and distilling at 120° C. under 0.06 mbar, 5.8 g of expected product is obtained in the form of a base. 110 cm³ of 0.1N hydrochloric acid is added to 1.5 g of the base obtained above, followed by concentrating to dryness and crystallizing from ethanol and ether. 1.45 g of expected hydrochloride is recovered. M.p.=202°-204° C.

Analysis: $C_9H_{12}N_2O$, HCl Calculated: C % 53.87 H % 6.53 N % 13.96; Found: 53.64 6.47 13.79.

EXAMPLE 6

3-(oxazol-2-yl)-1,2,5,6-tetrahydropyridine hydrochloride 4 g of 1-methyl-3-(oxazol-2-yl)-1,2,5,6-tetrahydropyridine in 80 cm³ of dichloroethane is cooled to −5° C. under inert atmosphere and 3.88 g of alpha-chloroethyl chloroformate is added. The mixture is heated under reflux for one hour 30 minutes, evaporated, the residue is taken up in diethylether, followed by filtering. The ethereal phase is concentrated, the residue is taken up in 30 cm³ of methanol, heated at boiling point for 40 minutes and evaporated to dryness. After crystallization from ethanol and ether, 2.1 g of expected product is obtained. M.p.=188°-191° C.

Analysis: $C_8H_{10}N_2O$, HCl Calculated: C % 51.48 H % 5.94 N % 15.01; Found: 51.65 5.87 15.24.

EXAMPLE 7

1-methyl-3-(5-methyloxazol-2-yl)-1,2,5,6-tetrahydropyridine and its hydrochloride

STAGE A 1-methyl-3-(5-methyloxazol-2-yl)-pyridinium iodide.

5 g of 3-(5-methyloxazol-2-yl)-pyridine prepared as indicated in Chimica Therap 4, 437 (1973) is dissolved in 50 cm³ of ethanol, 3 cm³ of iodomethane is added and the whole is heated under reflux for 10 hours. After cooling and decanting, ether is added, and after filtering, 8.68 g of product is obtained. M.p.=147°-148° C., after crystallization from ethanol.

Analysis: $C_{10}H_{11}N_2OI$ Calculated: C % 39.76 H % 3.67 N % 9.27; Found: 39.54 3.75 9.24.

STAGE B 1-methyl-3-(5-methyloxazol-2-yl)-1,2,5,6-tetrahydropyridine and its hydrochloride 1.6 g of sodium borohydride is added at −5°/−3° C. to 8.48 g of product obtained in Stage A in 110 cm³ of methanol. The reaction is continued with agitation for 2 hours at ambient temperature, the solvent is eliminated, the residue is taken up in water and extracted with ethyl acetate. After drying, the solvent is evaporated. After chromatography on silica (eluant: chloroform-methanol 9-1), distillation is carried out at 125°-130° C. under 0.07 mbar and 3.29 g of expected product is obtained in the form of a base. 64.5 cm³ of 0.1N hydrochloric acid is added to 1.15 g of the base obtained above, and after concentrating to dryness and crystallizing from methanol and ether, 1.24 g of expected hydrochloride is recovered.

M.p.=203°-205° C. (decomp.).

Analysis: $C_{10}H_{14}N_2O$, HCl Calculated: C % 55.94 H % 7.04 N % 13.05; Found: 55.71 7.22 13.01.

EXAMPLE 8

3-(5-methyloxazol-2-yl)-1,2,5,6-tetrahydropyridine hydrochloride 2.1 g of 1-methyl-3-(5-methyloxazol-2-yl)-1,2,5,6-tetrahydropyridine prepared as in Example 7 is dissolved under inert atmosphere in 25 cm³ of dichloromethane and 1.4 cm³ of alpha-chloroethyl chloroformate is added at 0° C. The mixture is heated under reflux for 2 hours, the solvent is eliminated, and the residue is taken up in ether. After filtering, the filtrate is concentrated to dryness, the residue is taken up in 20 cm³ of methanol with further heating under reflux for 40 minutes. After concentration to dryness and crystallization from isopropanol and ether, 2.06 g of expected product is recovered which is recrystallized from isopropanol/acetone. 1.42 g of product is obtained, melting at 182°-184° C.

Analysis: $C_9H_{12}N_2O$, HCl Calculated: C % 53.87 H % 6.53 N % 13.96; Found: 54.05 6.54 14.07.

EXAMPLE 9

1-benzoyloxy-3-(oxazol-2-yl)-1,2,5,6-tetrahydropyridine 2.5 g of 3-(oxazol-2-yl)-1,2,5,6-tetrahydropyridine hydrochloride prepared as in Example 6 and 3.22 g of potassium carbonate are added to a solution comprising 4.1 g of benzoyl peroxide in 30 cm³ of chloroform. After 2 hours of agitation at ambient temperature, then filtering, the filtrate is evaporated to dryness and the residue is purified by chromatography on silica (eluant: toluene-ethyl acetate 6-4). 2.4 g of product is obtained which is crystallized from cyclohexane.

M.p.=90°-92° C.

Analysis: $C_{15}H_{14}N_2O_3$ Calculated: C % 66.66 H % 5.22 N % 10.36; Found: 66.86 5.30 10.24.

EXAMPLE 10

1-hydroxy-3-(oxazol-2-yl)-1,2,5,6-tetrahydropyridine and its hydrochloride 5.4 g of product prepared as in Example 6 in 150 cm³ of ether is added to a solution comprising 0.65 g of sodium and 100 cm³ of methanol. After one hour of reaction at ambient temperature, the solvents are evaporated, the residue is taken up in dilute hydrochloric acid and extracted with ether. The acid phase is alkalized with sodium bicarbonate, then extracted with ethyl acetate. The extracts are purified by chromatography on alumina (eluant: chloroform-methanol 9-3). 3 g of expected product is obtained in the form of a base. 110 cm³ of 0.1N hydrochloric acid is added to 1.83 g of the base prepared above, followed by concentration to dryness. After crystallization from ethanol and ether, 1.3 g of expected crystallized hydrochloride is recovered, M.p.=158°-160° C., and 0.7 g of non-crystallizable hydrochloride is recovered.

Analysis: $C_8H_{10}N_2O_2$, HCl Calculated: C % 47.42 H % 5.47 N % 13.82; Found: 47.48 5.54 13.73.

EXAMPLE 11

Pharmaceutical composition

Tablets were prepared corresponding to the following formula:

| | |
|---|---|
| Product of Example 6 | 50 mg |
| Excipient q.s. for a tablet | 300 mg |

(Detail of excipient: lactose, talc, treated starch, rice starch, magnesium stearate).

EXAMPLE 12

Pharmaceutical composition

Capsules were prepared corresponding to the following formula:

| | |
|---|---|
| Product of Example 10 | 60 mg |
| Excipient q.s. for a capsule | 300 mg |

(Detail of excipient: talc, magnesium stearate, aerosil).

PHARMACOLOGICAL STUDY

Acute toxicity

The test is carried out on male mice ($CD_1$ Charles Rivers) of 22 to 24 g, without food for 16 hours. The products are administered by oral route at a dose of 1000, 500, 250, 125, 62 and 31 mg/kg. The mortality is noted during the 7 days following treatment.

| Product of Example | $LD_{50}$ in mg/kg |
|---|---|
| 2 | 125 |
| 6 | 200 |
| 8 | 500 |
| 10 | 300 |
| Aerocoline, HBr | 600 |

Test on the isolated ileum of a guinea-pig

Fragments of the ileum of guinea-pigs killed by decapitation are removed. The isolated ileum is placed in 10 cm³ of Tyrode's solution at 37° C. and aerated by a mixture of oxygen (95%) and carbon dioxide (5%). The contractions caused by the products are recorded using a sensor connected to a polygraph. The products under test are added, at concentrations comprised between $1.10^{-3}M$ and $1.10^{-8}M/l$.

The products presenting a contracting effect are tested vis-à-vis atropine and hexamethonium to establish if the activity is of "muscarinic" or "nicotinic" type.

The possible antagonist activity of the products is tested vis-à-vis acetylcholine.

The agonist activity is expressed in $pD_2$ (negative logarithm of the dose which produces 50% of the maximum effect).

| Product of Example | $pD_2$ |
|---|---|
| 2 | 5.97 |

| Product of Example | pD$_2$ |
| --- | --- |
| 6 | 5.71 |
| 8 | 5.23 |
| 10 | <4 |
| Aerocoline, HBr | 6.48 |

Diarrhoeic activity

The test is carried out on male mice (CD$_1$ Charles Rivers) weighing 25 to 30 g, without food for 6 hours. The product at 5% in methocel is administered by oral route, by means of an oesophagus probe.

Control animals receive only the excipient.

After treatment, the animals are put separately into cages, the bottom of which is covered with absorbent paper, and are observed for 30, 60, 120 and 180 minutes.

The sheets of absorbent paper are changed after each observation.

The consistency of the faeces is evaluated according to the Randall and Baruth method (Arch. Int. Pharmacodyn. 220, 94, (1976)) according to the following scale of values.

0: firm consistency,
1: slightly soft faeces with or without moist circle,
2: slightly soft faeces with presence of a well-defined moist circle,
3: soft faeces with presence of a large moist circle,
4: faeces without consistency with presence of a very large moist circle.

For each product, the dose is noted which causes diarrhoea in 50% of the animals according to the Miller and Tainter method (Proc. Soc. Exp. Biol. Med. 57, 261, (1944)).

| Product of Example | DE$_{50}$ in mg/kg |
| --- | --- |
| 2 | 3 |
| 6 | 15 |
| 10 | 10 |
| Aerocoline, HBr | 35 |

Hypothermic activity

The test is carried out on male mice (CD$_1$ Charles Rivers) weighing 25 to 30 g, without food for 6 hours.

The body temperature is noted by means of a thermocouple placed about 1.5 cm inside the rectum and connected to an electric temperature recorder.

The products are administered by oral or sub-cutaneous route and the temperatures are noted at 0 and 30 minutes, one hour, 2 hours and 2 hours 30 minutes after treatment.

The degree of hypothermia is evaluated as the difference between the treated animals and the controls and the dose necessary to reduce the body temperature by 1° C. is determined.

| Product of Example | Effective dose (−1° C.) in mg/kg | |
| --- | --- | --- |
| | O.R. | SC.R. |
| 2 | 2.6 | 1.7 |
| 6 | 3.2 | 3.2 |
| 8 | 24 | 25 |
| 10 | 4.2 | 4.1 |
| Aerocoline, HBr | 194 | 3 |

We claim:
1. A compound of formula (I):

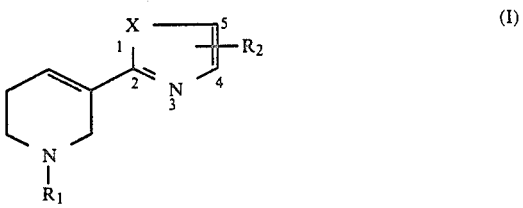

in which X represents oxygen or sulphur, R$_1$ represents hydroxy, R$_2$ represents hydrogen, a linear, branched or cyclic alkyl containing up to 6 carbon atoms, alkenyl or alkynyl containing up to 6 carbon atoms, an alkoxyalkyl alk'$_1$Oalk'$_2$ radical in which alk'$_1$ and alk'$_2$ represent alkyl containing up to 6 carbon atoms, hydroxyalkyl in which the alkyl contains up to 6 carbon atoms or aryl containing up to 14 carbon atoms, as well as its addition salts with organic or mineral acids.

2. The compound of formula (I) as defined in claim 1, in which X represents oxygen, as well as its addition salts with organic or mineral acids.

3. The compound of formula (I) as defined in claim 1, in which R$_2$ represents hydrogen, as well as its addition salts with organic or mineral acids.

4. The compound of formula (I) as defined in claim 1, in which R$_2$ represents a linear, branched or cyclic alkyl containing up to 6 carbon atoms, as well as its addition salts with organic or mineral acids.

5. The compound of formula (I) as defined in claim 4, in which R$_2$ represents methyl, as well as its addition salts with mineral or organic acids.

6. The compound of formula (I) as defined in claim 1, in which X represents sulphur and R$_2$ represents a linear, branched or cyclic alkyl containing up to 6 carbon atoms, as well as its addition salts with organic or mineral acids.

7. 1-hydroxy-3-(oxazol-2-yl)-1,2,5,6-tetrahydropyridine and its addition salts with organic or mineral acids.

8. A therapeutic composition for the treatment of Alzheimer's disease, senile dementia and memory disorders in the aged comprising a central cholinomimetically effective amount of compound (I) as defined in claim 1, and a pharmaceutically acceptable carrier.

9. A method for treating patients suffering from Alzheimer's disease, senile dementia or memory disorders of the aged comprising administering to the patient a cholinomimetically effective amount of compound (I) as defined in claim 1.

* * * * *